United States Patent [19]

Davis et al.

[11] Patent Number: 5,319,102
[45] Date of Patent: Jun. 7, 1994

[54] HETEROCYCLIC-ALKYLENE QUINOXALINYLOXYPHENOXYPROPANOATE HERBICIDES

[75] Inventors: Robert G. Davis, Naugatuck; Allyn R. Bell, Cheshire, both of Conn.; John A. Minatelli, Goshen, N.Y.

[73] Assignee: Uniroyal Chemical Company, Inc., Middlebury, Conn.

[21] Appl. No.: 876,614

[22] Filed: Apr. 30, 1992

Related U.S. Application Data

[63] Continuation of Ser. No. 378,357, Jul. 11, 1989, Pat. No. 5,120,348, which is a continuation-in-part of Ser. No. 141,182, Jan. 6, 1988, abandoned.

[51] Int. Cl.$^5$ .................. C07D 335/02; C07D 309/06; C07D 305/06
[52] U.S. Cl. ...................................... 549/28; 549/29; 549/30; 549/39; 549/323; 549/420; 549/427; 549/454; 549/475; 549/499; 549/511
[58] Field of Search ............................ 544/354; 71/92; 549/499, 23, 28, 29, 30, 39, 323, 420, 427, 454, 475, 511

[56] References Cited

U.S. PATENT DOCUMENTS

| | | | |
|---|---|---|---|
| 4,227,009 | 10/1980 | Koch et al. | 71/88 |
| 4,429,167 | 1/1984 | Lee | 568/636 |
| 4,499,271 | 2/1985 | Kohn et al. | 71/94 |
| 4,562,273 | 12/1985 | Le Bigot et al. | 549/499 |
| 4,564,381 | 1/1986 | Bieringer et al. | 71/88 |
| 4,601,748 | 7/1986 | Kruger et al. | 71/94 |
| 4,609,396 | 9/1986 | Fawzi | 71/92 |
| 4,629,493 | 12/1986 | Ura et al. | 71/92 |
| 4,750,931 | 6/1988 | Rogers et al. | 544/354 |
| 5,120,348 | 6/1992 | Davis et al. | 544/354 |

FOREIGN PATENT DOCUMENTS

| | | |
|---|---|---|
| 46467 | 3/1982 | European Pat. Off. . |
| 288275 | 10/1988 | European Pat. Off. . |
| 323727 | 7/1989 | European Pat. Off. . |

OTHER PUBLICATIONS

Hanasaki et al "Preparation of N-(3-alkoxyphenyl) tetrahydrophthalimides as Herbicides" CA 112(7) 55598n 1989.
Someya et al "Preparation of Phenoxypropionic Acid Derivatives for use as Herbicides" CA 110(17) 154321g 1988.
Ebner "Phenoxyphenoxycarboxylic Acid Ester Derivatives with Herbicidal and Plant Growth Regulating Properties" CA 94(25) 208711f 1980.
Sucky "Pesticidal p-phenoxyphenoxyalkanecarboxylic Acid Esters" CA 89(25) 215059z 1977.
Abstract for EP206772 (Dec. 30, 1986).
Abstract for ES542418 (Apr. 16, 1986).
Abstract for EP113831 (Jul. 25, 1984).
Abstract for EP121871 (Oct. 17, 1984).
Abstract for DE 3433390 (Mar. 20, 1986).
Derwent 91-033749/05, Abstract of Japanese Patent Publication 2304077 (May 1989).
Nissan Chemical Industries Ltd. (Chem. Abs. vol. 98: 198278m) (1983).

Primary Examiner—C. Warren Ivy
Assistant Examiner—A. A. Owens
Attorney, Agent, or Firm—Jerome D. Drabiak

[57] ABSTRACT

Heterocyclic-alkylene quinoxalinyloxyphenoxypropanoate compounds exhibit unexpectedly desirable selective herbicidal activity. Also disclosed are compositions comprising such compounds as well as a method of controlling the growth of undesirable plants employing such compounds.

5 Claims, No Drawings

HETEROCYCLIC-ALKYLENE QUINOXALINYLOXYPHENOXYPROPANOATE HERBICIDES

CROSS REFERENCE TO RELATED APPLICATION

This is a continuation of application Ser. No. 07/378,357 filed Jul. 11, 1989 now U.S. Pat. No. 5,120,348 which was a continuation-in-part of application Ser. No. 07/141,182 filed Jan. 6, 1988, now abandoned.

FIELD OF THE INVENTION

This invention is directed to novel heterocyclicalkylene quinoxalinyloxyphenoxypropanoate compounds which exhibit unexpectedly desirable selective herbicidal activity. In other aspects, this invention is directed to herbicidal compositions comprising such compounds as well as to a method for controlling the growth of plants employing such quinoxalinyl derivatives.

BACKGROUND OF THE INVENTION

The control of undesirable grasses is important in the cultivation of many important broadleaf agricultural species such as soybeans, peanuts and cotton, as well as in the cultivation of many horticultural species. Moreover, the presence of such weeds on noncropped areas may present a fire hazard, or may result in the undesirable drifting of sand or snow or irritation to persons with allergies. Accordingly, it would be beneficial to control the growth of undesirable grasses, particularly in a manner which would allow for the selective control of such plants without concurrent injury to desirable broadleaf crops or vegetation.

Among the classes of compounds which have been employed in the past to control the growth of undesirable vegetation are certain quinoxalinyloxyphenoxy compounds. Thus, Ura et al in U.S. Pat. No. 4,629,493 disclose certain quinoxalinyl compounds, including 6-membered homocyclic ring derivatives such as benzyl 2-[4-(6-chloro-2-quinoxalinyloxy)phenoxy]-propanoate, which are useful as selective herbicides. Similarly, in European Patent Application 46,467, Ura et al show a number of quinoxalinyloxyphenoxy compounds, including a morpholino ester thereof, which are useful as herbicides.

Somewhat similarly, U.S. Pat. No. 4,429,167 to Lee discloses a broad range of 3-alkoxy-4-substituted-phenoxy-2,-3-unsaturated acids, including quinoxalinyl derivatives thereof which are selective herbicides for grasses, while U.S. Pat. No. 4,609,396 to Fawzi shows a variety of quinoxalinyloxy ethers which are useful for controlling grass weeds in broadleaf plants. Chemical Abstracts 98, 198278m (1983) discloses herbicidal glycidyl quinoxalin-2-yloxyphenoxypropionates while European Patent Application 206,772 shows quinoxalinyloxybenzyl ester compounds which are useful for the selective control of weeds in rice. Spanish Patent Application 8,603,431 shows herbicidal alkyl quinoxalinyloxyphenoxypropanoates while European Patent Application 113,831 shows selective herbicides which are carbamylethyl esters of quinoxalinyloxyphenoxypropanoic acids. European Patent Application 121,871 shows herbicidal phosphoric acid esters of quinoxalinyloxyphenoxypropanoates while U.S. Pat. No. 4,499,271 shows phosphoric acid esters of quinoxalinyloxyphenoxypropanoates. German Application 3,433,390 shows silane esters of quinoxalinyloxyphenoxypropanoic acid, while Kruger et al in U.S. Pat. No. 4,601,748 disclose herbicidal 2-phenoxypropionic acid derivatives of pentitols.

In contrast, U.S. Pat. No. 4,564,381 to Bieringer et al shows a very broad class of compounds, including many quinoxalinyloxyphenoxypropanoic esters which function as plant growth stimulants.

While many of the compounds shown in the above publications exhibit desirable herbicidal activity, it would nevertheless be desirable to possess herbicides which exhibited enhanced selective control of undesirable grasses.

Accordingly, it is an object of this invention to provide a class of novel compounds which exhibit unexpectedly desirable selective herbicidal activity.

It is a further object of this invention to provide a method of controlling undesirable weeds.

These objects and other additional objects will become more fully apparent from the following disclosure and accompanying examples.

DESCRIPTION OF THE INVENTION

In one aspect, this invention is directed to a novel class of compounds having the structural formula:

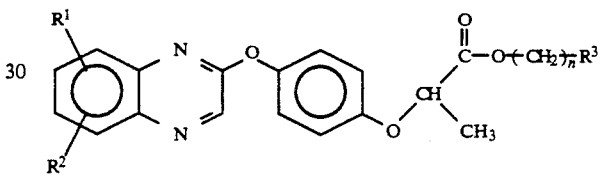

wherein:
n is 0, 1, 2 or 3;
$R^1$ and $R^2$ are each independently selected from the group consisting of halogen, hydrogen, $C_1$-$C_3$ alkoxy, $C_1$-$C_3$ haloalkoxy, monohalomethyl, dihalomethyl, trihalomethyl, cyanato and nitro; and
$R^3$ is a 4-, 5- or 6-membered saturated, unsaturated or partially unsaturated heterocyclic ring containing 1 or 2 oxygen atoms, or a 5- or 6-membered saturated, unsaturated or partially unsaturated heterocyclic ring containing 1 or 2 sulfur atoms or one sulfur atom and one oxygen atom; said ring optionally being substituted with between 1 and 3 substituents each independently selected from the group consisting of oxo, $C_1$-$C_3$ alkyl and $C_1$-$C_3$ alkoxy.

In another aspect, this invention is directed to a herbicidal composition comprised of:
(A) a compound having the structural formula:

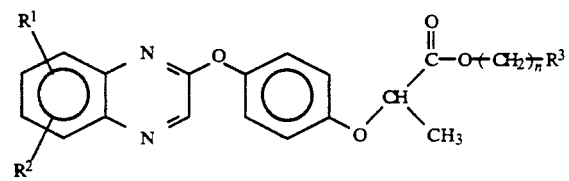

wherein:
n is 0, 1, 2 or 3;
$R^1$ and $R^2$ are each independently selected from the group consisting of halogen, hydrogen, $C_1$-$C_3$ alkoxy, $C_1$-$C_3$ haloalkoxy, monohalomethyl, dihalomethyl, trihalomethyl, cyanato and nitro; and $R^3$ is a 4-, 5- or 6-membered saturated, unsaturated or partially unsaturated heterocyclic ring containing 1 or 2 oxygen atoms, or a 5- or 6-membered saturated, unsaturated or partially unsaturated heterocyclic ring containing 1 or 2 sulfur atoms or one sulfur atom and one oxygen atom; said ring optionally being substituted with between 1 and 3 substituents each independently selected from the group consisting of oxo, $C_1$-$C_3$ alkyl and $C_1$-$C_3$ alkoxy, and (B) a suitable carrier.

In yet another aspect, this invention is directed to a method of controlling undesirable plants, which method comprises applying to the locus of such undesirable plants a herbicidally effective amount of a compound having the structural formula:

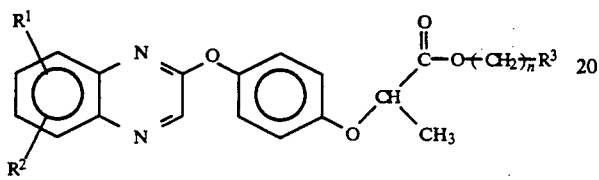

wherein:

n is 0, 1, 2 or 3;

$R^1$ and $R^2$ are each independently selected from the group consisting of halogen, hydrogen, $C_1$-$C_3$ alkoxy, $C_1$-$C_3$ haloalkoxy, monohalomethyl, dihalomethyl, trihalomethyl, cyanato and nitro; and $R^3$ is a 4-, 5- or 6-membered saturated, unsaturated, or partially unsaturated heterocyclic ring containing 1 or 2 oxygen atoms, or a 5- or 6-membered saturated, unsaturated or partially unsaturated heterocyclic ring containing 1 or 2 sulfur atoms or one sulfur atom and one oxygen atom; said ring optionally being substituted with between 1 and 3 substituents each independently selected from the group consisting of oxo, $C_1$-$C_3$ alkyl and $C_1$-$C_3$ alkoxy.

The novel compounds of this invention are of the formula:

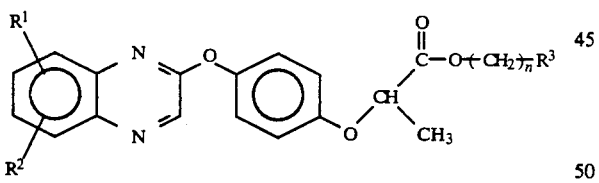

wherein $R^1$, $R^2$, $R^3$ and n are as defined for formula (I) above. It is to be noted that $R^3$ may be an unsaturated, saturated or partially unsaturated (i.e., containing at least one carbon-carbon double bond and at least one carbon-carbon single bond) heterocyclic moiety.

Preferably:

$R^1$ is chlorine, trichloromethyl or trifluoromethyl;
$R^2$ is hydrogen; and
$R^3$ is furanyl, tetrahydrofuranyl, dioxolanyl, tetrahydrodioxolanyl, dihydropyranyl, tetrahydropyranyl, tetrahydrothiophenyl, tetrahydrothiophenyl-1,1-dioxide, tetrahydrothiopyranyl, (thiophenyl)-methyl, (thiophenyl)ethyl, (dimethyloxathiophenyl)methyl, (dimethyldithiolanyl)methyl or thiochromanyl; optionally substituted with 1, 2 or 3 moieties selected from the group consisting of oxo and methyl.

Particularly preferred compounds include:

2-tetrahydrofuranylmethyl 2-[4-(6-chloro-2-quinoxalinyloxy)phenoxy]-propanoate;

2-furanylmethyl 2-[4-(6-chloro-2-quinoxalinyloxy)-phenoxy]propanoate;

2-tetrahydropyranylmethyl 2-[4-(6-chloro-2-quinoxalinyloxy)-phenoxy]-propanoate;

2-[2-(2-methyl-1,3-dioxolanyl)]ethyl 2-[4-(6-chloro-2-quinoxalinyloxy)phenoxy]propanoate;

4-(2,2-dimethyl-1,3-dioxolanyl)methyl 2-[4-(6-chloro-2-quinoxalinyloxy)phenoxy]propanoate;

3-tetrahydrothiophenyl 2-[4-(6-chloro-2-quinoxalinyloxy)phenoxy]propanoate;

4-tetrahydrothiopyranyl 2-[4-(6-chloro-2-quinoxalinyloxy)phenoxy]propanoate;

3-tetrahydrothiopyranyl 2-[4-(6-chloro-2-quinoxalinyloxy)phenoxy]propanoate;

3-tetrahydrothiophenyl-1,1-dioxide 2-[4-(6-chloro-2-quinoxalinyloxy)phenoxy]propanoate;

2-thiophenylmethyl 2-[4-(6-chloro-2-quinoxalinyloxy) phenoxy]propanoate;

2-(2-thiophenyl)ethyl 2-[4-(6-chloro-2-quinoxalinyloxy)phenoxy]propanoate;

5-(2,2-dimethyl-1,3-oxathiolanyl)methyl 2-[4-(6-chloro-2-quinoxalinyloxy)phenoxy]propanoate;

4-(2,2-dimethyl-1,3-dithiolanyl)methyl 2-[4-(6-chloro-2-quinoxalinyloxy)phenoxy]propanoate; and 4-thiochromanyl 2-[4-(6-chloro-2-quinoxalinyloxy)-phenoxy]propanoate.

The compounds of this invention may be prepared by reacting a quinoxalinyloxyphenol compound of the formula:

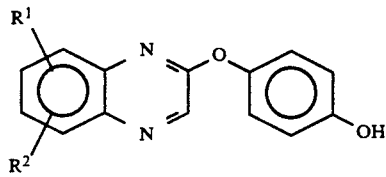

wherein $R^1$ and $R^2$ are as defined for structure (I) above; with a substituted heterocyclicalkylpropanoate of the formula:

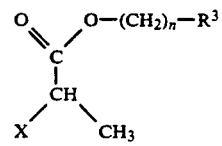

wherein X is halogen, mesylate or tosylate and n and $R^3$ are as defined for structure (I) above. This reaction is typically conducted in an organic solvent (such as dimethylformamide, dimethylsulfoxide, acetonitrile or the like) in the presence of an inorganic or organic base (such as sodium carbonate, potassium hydroxide or potassium carbonate) at suitable temperature.

The quinoxalinyloxyphenoxy starting materials may be prepared by reacting a 2-haloquinoxaline compound having the formula:

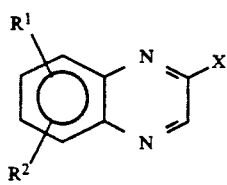

wherein

X is halogen and $R^1$ and $R^2$ are as defined in structure (I) above, with a phenyl benzyl ether of the formula:

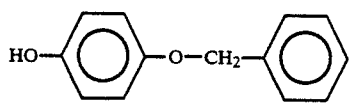

in the presence of an inorganic or organic base to produce an intermediate of the formula:

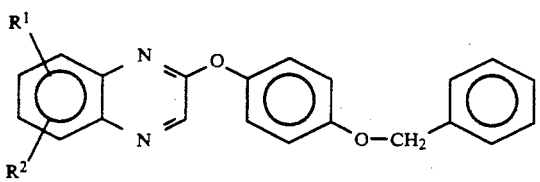

and hydrogenating such intermediate (employing a hydrogenation catalyst such as palladium) to produce a debenzylation thereby forming the quinoxalinyloxyphenol starting material.

The heterocyclicalkylpropanoate starting material may be produced by reacting a halogenated propionic acid halide with the appropriate heterocyclic alkyl alcohol.

Alternatively ethyl 2-halopropanoate may be reacted with the appropriate heterocyclic alkyl alcohol in the presence of an appropriate catalyst (such as tetra-isopropoxy titanium) to produce the heterocyclicalkylpropanoate halide via a transesterification process.

The compositions of this invention are comprised of (A) at least one of the quinoxalinyloxyphenoxypropanoate compounds of this invention, and (B) a suitable carrier.

To prepare such herbicidal compositions, the quinoxalinyloxyphenoxypropanoate compound may be mixed with inert ingredients to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, any of which could be made by one familiar with the art. For instance, the active compound may be impregnated on finely-divided or granular inorganic or organic carriers such as attapulgite clay, sand, vermiculite, corn cob, activated carbon or other granular carriers known to the art. The impregnated granules may then be spread on the soil or incorporated into the soil.

Alternatively, the chemical may be formulated as a wettable powder by mixing it with an inactive powdered carrier to which a surface active dispersing agent has been added and grinding the mixture into a fine powder. Typical powdered solid carriers are the various mineral silicates (such as mica, talc, pyrophyllite, clays and the like) or powdered organic material (e.g., corn cob). The wettable powder may then be dispersed in water and sprayed on the soil surface, or on crop or weed plants.

Similarly, an emulsifiable concentrate may be prepared by dissolving the chemical in a solvent such as xylene, toluene, or other aliphatic or aromatic hydrocarbon to which a surface active dispersing agent generally has been added. The emulsifiable concentrate may then be dispersed in water and applied-by spraying.

The concentration of active chemical in the composition may vary widely typically ranging from about 1 to about 95% by weight. The concentration of active chemical in dispersions applied to the soil, seed or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Suitable adjuvants containing appropriate surface active agents include "AGRI-DEX" and "INDUCE" (Helena Chemical Co.), "SUPER SAVOL" (Leffingwell), "CANPLUS 411" (Atlas), and "ASSIST" (BASF). Similarly, such formulations may be applied to the soil either as a liquid or a granule.

For use as a preemergence herbicide the compound of this invention is typically applied at a rate of from about 0.01 to about 10 pounds per acre (about 0.01 to about 11.2 kg/ha) to soil which contains weed and crop seed. Such application is made either to the surface of the soil or into the upper one to three inches (2.5 to 7.5 cm.) of soil. When employed as a postemergence herbicide the compound is typically applied at a rate of from about 0.01 to about 10 pounds per acre (about 0.01 to about 11.2 kg/ha) to the aerial portions of weeds.

The most suitable dosage of application, and the most effective type and amount of adjuvant substance will depend on a number of factors, including the plant species; the stage of plant development; the method of application; the air and soil temperature and the quantity and intensity of rainfall before and after treatment; the soil type, pH, fertility and moisture and organic matter content; the physiological condition and vigor of the target plants; the relative humidity and wind velocity of the air around the crop at the time of treatment; the extent and density of the foliar canopy of the target plant; the light quality, intensity and duration each day; the type and interval of previous and subsequent crop protectant chemical applications. However, one skilled in the art can, by routine experimentation, readily determine optimum conditions for the employment of any particular quinoxyalinyloxyphenoxypropanoate compound.

The compounds of the present invention include the isomeric forms and mixtures thereof. Thus, the invention includes the optically active isomers and racemic mixtures. Unless otherwise specified herein, the compounds described in the examples are racemic mixtures.

EXAMPLES

The following Examples are intended to further illustrate the invention and are not intended to limit the scope of the invention in any manner whatsoever.

EXAMPLE 1

Preparation of 2-tetrahydrofuranylmethyl 2-[4-(6-chloro-2-quinoxalinyloxy)phenoxy]propanoate (Compound Number 4).

A. Preparation of 2-tetrahydrofuranylmethyl 2-bromopropanoate

To a 250 milliliter three-necked flask were added 0.15 mole of 2-(hydroxymethyl)tetrahydrofuran, 0.15 mole of triethylamine, and 100 milliliters of diethylether. The flask was immersed in ice, and 0.15 mole of 2-bromopropanoyl chloride introduced dropwise. The ice bath was removed, and the reaction stirred at ambient temperature for two hours. The mixture was extracted with an equal volume of water, and the organic phase dried over sodium sulfate. Decantation and solvent removal resulted in 2-tetrahydrofuranylmethyl 2-bromopropanoate in 94% yield.

B. Preparation of 2-tetrahydrofuranylmethyl 2-[4-(6-chloro-2-quinoxalinyloxy)-phenoxy]propanoate To a 500 milliliter roundbottom flask were added 0.055 mole of 2-(4-hydroxyphenoxy)-6-chloroquinoxaline, 0.055 mole of 2-tetrahydrofuranylmethyl 2-bromopropanoate, 0.110 mole of anhydrous potassium carbonate, and 250 milliliters of acetonitrile. The mixture was refluxed for 5.5 hours and the solvent removed. The residue was filtered through a column of alumina with dichloromethane. Solvent removal and recrystallization from boiling hexane resulted in an 85% yield of 2-tetrahydrofuranylmethyl 2-[4-(6-chloro-2-quinoxalinyloxy)phenoxy]propanoate. The material melted over a range of 52–55° C.

EXAMPLE 2

Preparation of 2-thiophenylmethyl 2-[4-(6-chloro-2-quinoxalinyloxy)phenoxy]propanoate (Compound Number 11).

A. Preparation of 2-thiophenylmethyl 2-bromopropanoate

To a 50 milliliter three-necked flask equipped with stir bar, glass stopper, rubber stopple, connecting tube, and nitrogen atmosphere were added 2.1808 grams (0.0191 moles) of 2-hydroxymethylthiophene, 2.66 milliliters (0.0191 moles of triethylamine, and 20 milliliters of anhydrous diethylether.

The flask was immersed in an ice water bath, and 2.0 milliliters (0.0191 moles) of 2-bromopropanoyl bromide added dropwise by syringe. The mixture was stirred at 0° for 5 minutes, then at ambient temperature for one hour. Triethylamine hydrochloride was removed by filtration on a Buchner funnel and with two water extractions of the organic phase. Drying of the ether solution over anhydrous sodium sulfate, decantation, and solvent removal by rotary evaporation resulted in a quantitative yield of 2-thiophenylmethyl 2-bromopropanoate as an oil.

B. Preparation of 2-thiophenylmethyl 2-[4-(6-chloro-2-quinoxalinyloxy)phenoxyl]propanoate To a 250 milliliter roundbottom flask equipped with stir bar, reflux condenser, connecting tube, and nitrogen atmosphere were added 4.3781 grams (0.0161 moles) of 2-(4-hydroxyphenoxy)-6-chloroquinoxaline, 4.000 grams (0.0161 moles) of 2-thiophenylmethyl 2-bromopropanoate, 4.4377 grams (0.0321 moles) of anhydrous potassium carbonate, and 100 milliliters of acetonitrile.

The mixture was refluxed for 6 hours, then filtered while hot through a Buchner funnel. Acetonitrile was removed by rotary evaporation, and the residue plug filtered through a column of alumina with dichloromethane. Solvent removal at reduced pressure resulted in 4.6389 grams of tan solid 2-thiophenylmethyl 2-[4-(6-chloro-2-quinoxalinyloxy)phenoxy]propanoate, a 65.3% yield.

EXAMPLE 3

Additional compounds within the scope of the invention were prepared using essentially the procedures outlined above. The structures and melting points are summarized in Table I below. The NMR spectra of compounds 3, 5 and 7–18 are summarized in Table II below. (Note: in such NMR data s=singlet; d=duplet; t=triplet; q=quartet; and m=multiplet).

TABLE I $$R^1 \text{-quinoxaline-O-phenyl-O-CH(CH}_3\text{)-C(=O)-O-(CH}_2\text{)}_n\text{-R}^3$$

| Compound Number | $R^1$ | $R^2$ | $R^3$ | n | Melting Point (°C.) |
| --- | --- | --- | --- | --- | --- |
| 1 | 6-Cl | H | 2,2-dimethyl-4-oxo-1,3-dioxolanyl (CH₃, CH₃, =O) | 1 | 130–134° |
| 2 | 6-Cl | H | 2-furyl | 1 | 98–101° |
| 3 | 6-Cl | H | 2,2-dimethyl-1,3-dioxolanyl | 1 | Oil |
| 4 | 6-Cl | H | 2-tetrahydrofuranyl | 1 | 52–55° |
| 5 | 6-Cl | H | 2-methyl-1,3-dioxolanyl (CH₃) | 2 | Oil |
| 6 | 6-Cl | H | 2-tetrahydropyranyl | 1 | 60–64° |
| 7 | 6-Cl | H | 2-tetrahydropyranyl | 0 | 78–82° |

TABLE I-continued

R¹, R² substituted quinoxaline structure:

C(=O)−O−(CH₂)ₙ−R³ ester with CH(CH₃) and O-phenyl-O linkage to quinoxaline

| Compound Number | R¹ | R² | R³ | n | Melting Point (°C.) |
|---|---|---|---|---|---|
| 8 | 6-Cl | H | tetrahydrofuran-2-yl (O in ring) | 0 | Oil |
| 9 | 6-Cl | H | 3,3-dimethyloxetane (CH₃ substituted, O in ring) | 1 | Oil |
| 10 | 6-Cl | H | tetrahydrothiophen-2-yl (S in ring) | 0 | Oil |
| 11 | 6-Cl | H | tetrahydrothiopyran-2-yl (S in 6-ring) | 0 | Oil |
| 12 | 6-Cl | H | tetrahydrothiopyran-3-yl (S in 6-ring) | 0 | Oil |
| 13 | 6-Cl | H | tetrahydrothiophene-SO₂ | 1 | Oil |
| 14 | 6-Cl | H | thiophen-2-yl | 1 | 112–114° |
| 15 | 6-Cl | H | thiophen-2-yl | 2 | 171–172° |
| 16 | 6-Cl | H | 2,2-dimethyl-1,3-oxathiolane (H₃C, CH₃, O, S) | 1 | Oil |
| 17 | 6-Cl | H | 2,2-dimethyl-1,3-dithiolane (H₃C, CH₃, S, S) | 1 | Oil |
| 18 | 6-Cl | H | 2,3-dihydrobenzothiophen-3-yl | 0 | Oil |

TABLE II

Nuclear Magnetic Resonance Data

TABLE II

| Compound Number | 8/25 Nuclear Magnetic Resonance Data NMR(CDCl₃) |
|---|---|
| 3 | 1.38(s, 3H), 1.43(s, 3H), 1.68(d, 3H), 3.50–4.24(m, 5H), 4.80(q, 1H), 7.02(q, 4H), 7.59(s, 2H), 8.00(s, 1H), 8.61(s, 1H). |
| 5 | 1.46(s, 3H), 1.77(d, 3H), 2.14(t, 2H), 3.99(s, 4H), 4.38(t, 2H), 4.81(q, 1H), 7.07(q, 4H), 7.62(s, 2H), 8.02(s, 1H), 8.62(s, 1H). |
| 8 | 1.64(d, 3H), 3.70–3.96(m, 5H), 4.78(q, 1H), 5.38(s, 1H), 6.92–7.20(q, 4H), 7.54–7.68(m, 2H), 8.02(s, 1H), 8.65(s, 1H). |
| 9 | 1.21(s, 3H), 1.60(d, 3H), 4.08–4.48(m, 6H), 4.78(q, 1H), 6.76–7.18(q, 4H), 7.48(m, 2H), 7.88(s, 1H), 8.52(s, 1H). |
| 10 | 1.63(d, 3H), 1.88–2.35(m, 2H), 2.73–3.18(m, 4H), 4.79(q, 1H), 5.57(m, 1H), 6.96(d, 2H), 7.20(d, 2H), 7.63(m, 2H), 8.03(s, 1H), 8.65(s, 1H). |
| 11 | 1.65(d, 3H), 1.70–2.19(m, 4H), 2.46–2.87(m, 4H), 4.78(q, 1H), 4.95(m, 1H), 6.95(d, 2H), 7.08(d, 2H), 7.63(m, 2H), 8.03(s, 1H), 8.67(s, 1H). |
| 12 | 1.65(d, 3H), 1.77–2.21(m, 4H), 2.45–2.82(m, 4H), 4.77(q, 1H), 4.98(s, 1H), 6.96(d, 2H), 7.17(d, 2H), 7.63(m, 2H), 8.04(s, 1H), 8.65(s, 1H). |
| 13 | 1.63(d, 2H), 2.47(m, 2H), 2.94–3.27(m, 4H), 4.85(q, 1H), 5.59(m, 1H), 6.96(d, 2H), 7.22(d, 2H), 7.60(m, 2H), 8.01(s, 1H), 8.65(s, 1H). |
| 14 | 1.64(d, 3H), 4.75(q, 1H), 5.32(s, 2H), 6.73–7.37(m, 7H), 7.55(m, 2H), 7.97(s, 1H), 8.57(s, 1H). |
| 15 | 1.69(d, 3H), 3.19(t, 2H), 4.42(t, 2H), 4.78(q, 1H), 6.71–7.31(m, 7H), 7.52(m, 2H), 7.96(s, 1H), 8.58(s, 1H). |
| 16 | 1.61(d, 3H), 1.67(s, 6H), 2.98(m, 2H), 4.38(m, 3H), 4.83(q, 1H), 6.96(d, 2H), 7.19(d, 2H), 7.62(m, 2H), 8.02(s, 1H), 8.67(s, 1H). |
| 17 | 1.57–1.82(m, 9H), 2.91–3.12(M, 2H), 4.11–4.39(m, 3H), 4.80(q, 1H), 6.95(d, 2H), 7.18(d, 2H), 7.63(m, 2H), 8.03(s, 1H), 8.66(s, 1H). |
| 18 | 1.62(d, 3H), 4.77(q, 1H), 6.08(m, 1H), 6.87–7.18(m, 4H), 6.91(d, 2H), 7.15(d, 2H), 7.61(M, 2H), 8.02(s, 1H), 8.63(s, 1H). |

EXAMPLE 4

Preemergence Control

To illustrate the effectiveness of the heterocyclicalkylene quinoxalinyloxyphenoxypropanoate compounds of this invention as preemergence herbicides, 300 mg of each of the below listed compounds were dissolved in 10 ml acetone to which 30 mg of an emulsifying agent, ethoxylated sorbitan monolaurate, were added. The solution was diluted to 100 ml with distilled water. Ten milliliters of this 3000 ppm solution were diluted to 250 ppm with distilled water. The chemical was applied at the rate of 10 lb/A (11.2 kg/ha) by drenching 46 ml of the 250 ppm solution on the surface of soil in 4-½ inch (11.25 cm.) plastic pots wherein seeds of the following weeds had been planted; velvet leaf (*Abutilon theophrasti* Medic.), "VL"; jimsonweed (*Datura stramonium* L.), "JW", or prickly sida (*Sida spinosa* L.), "PS"; tall morningglory (*Ipomea purpurea* L. Roth), "TM"; switchgrass (*Panicum virgatum* L.), "SG"; barnyard grass (*Echinolchloa crus-galli* (L.) Beauv.), "BG"; and green foxtail (*Setaria viridis*) (L.) Beauv. ), "GF".

The percent control of the weeds compared to untreated checks was determined two weeks after treatment. The results of such testing are summarized in Table III below.

TABLE III

Preemergent Control

| Compound Number | VL | JW | PS | TM | BG | SG | GF |
|---|---|---|---|---|---|---|---|
| 1 | 0 | 0 | — | 0 | 100 | 100 | 100 |
| 2 | 0 | 0 | — | 0 | 100 | 100 | 100 |
| 3 | 0 | 0 | — | 0 | 100 | 100 | 100 |
| 4 | 0 | 0 | — | 0 | 100 | 100 | 100 |
| 5 | 0 | 0 | — | 0 | 100 | 100 | 100 |
| 6 | 0 | 0 | — | 0 | 100 | 100 | 100 |
| 7 | 0 | 0 | — | 0 | 100 | 100 | 100 |
| 8 | 0 | 0 | — | 0 | 100 | 100 | 100 |
| 9 | 0 | 0 | — | 0 | 100 | 100 | 100 |
| 10 | 0 | — | 0 | 0 | 100 | 100 | 100 |
| 11 | 0 | — | 95 | 0 | 100 | 100 | 100 |
| 12 | 0 | — | 0 | 0 | 100 | 100 | 100 |
| 13 | 0 | — | 0 | 0 | 100 | 100 | 100 |
| 14 | 60 | 50 | — | 75 | 100 | 100 | 100 |
| 15 | 65 | 40 | — | 15 | 100 | 100 | 100 |
| 16 | 0 | — | 100 | 0 | — | 100 | 100 |
| 17 | 0 | — | 0 | 0 | 100 | 100 | 100 |
| 18 | 0 | — | 100 | 50 | 100 | 100 | 100 |

The above data show the excellent selective preemergent herbicidal control exhibited by the compounds of this invention.

EXAMPLE 5

Postemergence Control

To illustrate the effectiveness of the compounds of this invention as postemergence herbicides, the 3000 ppm solutions described under Example 4 were atomized with a conventional DeVilbiss [trademark] sprayer, wetting the foliage to the drip point. The remainder of the procedure was the same as described under Example 4. The weeds, which were the same species as described under Example 4, were treated six days after emergence.

The percent weed control was evaluated two weeks after treatment. The results of such testing are summarized in Table IV below.

TABLE IV

Postemergence Treatment

| Compound Number | VL | JW | PS | TM | BG | SG | GF |
|---|---|---|---|---|---|---|---|
| 1 | 0 | 0 | — | 0 | 100 | 100 | 100 |
| 2 | 0 | 0 | — | 15 | 100 | 100 | 100 |
| 3 | 10 | 90 | — | 15 | 100 | 100 | 100 |
| 4 | 0 | 20 | — | 10 | 100 | 100 | 100 |
| 5 | 0 | 0 | — | 40 | 100 | 100 | 100 |
| 6 | 0 | 20 | — | 10 | 100 | 100 | 100 |
| 7 | 0 | 0 | — | 5 | 100 | 100 | 100 |
| 8 | 0 | 0 | — | 5 | 100 | 100 | 100 |
| 9 | 0 | 0 | — | 5 | 100 | 100 | 100 |
| 10 | 30 | — | 0 | 50 | 100 | 100 | 100 |
| 11 | 40 | — | 15 | 20 | 100 | 100 | 100 |
| 12 | 0 | — | 0 | 10 | 100 | 100 | 100 |
| 13 | 0 | — | 20 | 60 | 100 | 100 | 100 |
| 14 | 15 | 30 | — | 0 | 100 | 100 | 100 |
| 15 | 30 | 35 | — | 10 | 100 | 100 | 100 |
| 16 | 100 | — | 65 | 40 | 100 | 100 | 100 |
| 17 | 10 | — | 0 | 5 | 100 | 100 | 100 |
| 18 | 0 | — | 0 | 0 | 100 | 100 | 100 |

The above data show the desirable selective postemergent herbicidal control exhibited by the novel compounds of this invention.

EXAMPLE 6

To illustrate the effectiveness of the novel heterocyclicalkylene quinoxalinyloxyphenoxypropanoate derivatives of this invention for preemergence grass control relative to prior art: homocyclicalkylene quinoxalinyloxyphenoxypropanoate compounds, solutions of several of the compounds were prepared in a manner similar to that described in Example 1. The 250 ppm solutions were diluted to 3.1 ppm with distilled water to provide testing at a rate of 0.14 kg/ha as a 46 ml drench to 11.25 cm diameter pots. In a similar manner, solutions of Compound A—benzyl 2-[4-(6-chloro-2-quinoxalinyloxy)phenoxy]propanoate, a compound within the scope of U.S. Pat. No. 4,629,493 (Compound 55)—were prepared and tested.

The structures of the tested compounds are as follows:

Compound Number 2

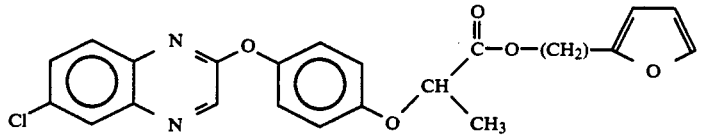

Compound Number 4

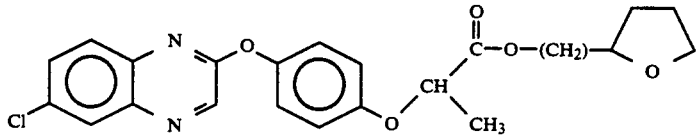

Compound Number 6

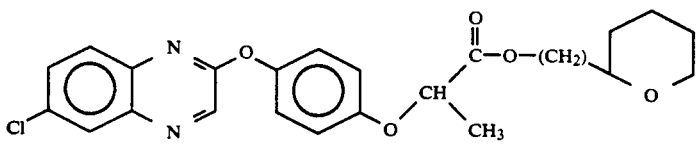

Compound A

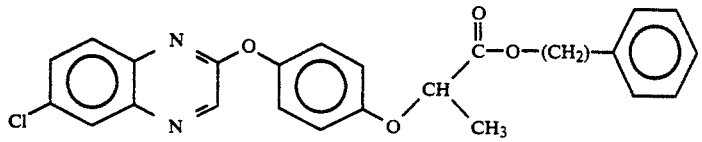

The results of such testing are summarized in Table V below.

TABLE V

| Compound | Rate kg/ha | Percent Weed Control | | |
|---|---|---|---|---|
| | | Wild Oats | Green Foxtail | Barnyard Grass |
| 2 | 0.14 | 60 | 80 | 60 |
| 4 | 0.14 | 70 | 80 | 80 |
| 6 | 0.14 | 50 | 70 | 90 |
| A | 0.14 | 50 | 65 | 30 |

The above data clearly show the unexpected desirable activity of the compounds of the present invention relative to known homocyclic 5- or 6-membered ring derivatives.

What is claimed is:

1. A compound having the structural formula

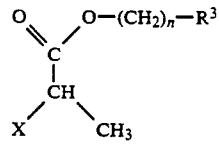

wherein:

n is 0, 1, 2, or 3;

$R^3$ is a 4-, 5- or 6-membered saturated, unsaturated or partially unsaturated heterocyclic ring having 1 or 2 oxygen atoms, or a 5- or 6-membered saturated, unsaturated or partially unsaturated heterocyclic ring having 1 or 2 sulfur atoms or one sulfur atom and one oxygen atom; said ring having no nitrogen atoms and optionally being substituted with between 1 and 3 substituents each independently selected from the group consisting of oxo, $C_1$-$C_3$ alkyl and $C_1$-$C_3$ alkoxy; X is halogen, mesylate or tosylate;

with the proviso that $R^3$ is not tetrahydropyran-2-yl, 2-furanone or 4,4-dimethyl-2-furanone.

2. The compound of claim 1 wherein n is 1; $R^3$ is tetrahydrofuranyl; and X is tosylate.

3. The compound of claim 1 wherein n is 1; $R^3$ is tetrahydrofuranyl; and X is halogen.

4. The compound of claim 3 wherein X is chlorine.

5. The compound of claim 3 wherein X is bromine.

* * * * *